United States Patent
Barde et al.

(10) Patent No.: US 6,935,780 B2
(45) Date of Patent: Aug. 30, 2005

(54) MEDICAL APPARATUS HAVING A SUPPORT TABLE FOR TREATMENT AND/OR EXAMINATION OF A SUBJECT THEREON

(75) Inventors: Karlheinz Barde, Speichersdorf (DE); Dieter Heinl, Erbendorf (DE); Thomas Schöcklmann, Kemnath (DE); Kerstin Waldbach, Porstendorf (DE)

(73) Assignee: Siemens Aktiengesellschaft (DE)

( * ) Notice: Subject to any disclaimer, the term of this patent is extended or adjusted under 35 U.S.C. 154(b) by 234 days.

(21) Appl. No.: 10/311,116
(22) PCT Filed: Jun. 5, 2001
(86) PCT No.: PCT/DE01/02102
§ 371 (c)(1),
(2), (4) Date: Dec. 16, 2002
(87) PCT Pub. No.: WO01/95807
PCT Pub. Date: Dec. 20, 2001

(65) Prior Publication Data
US 2003/0142791 A1 Jul. 31, 2003

(30) Foreign Application Priority Data
Jun. 15, 2000 (DE) .......................... 100 29 429

(51) Int. Cl.[7] .............................. A61B 6/04
(52) U.S. Cl. .............. 378/209; 5/635; 5/608; 5/601
(58) Field of Search ................. 378/208–210, 378/20, 68, 69, 177, 195; 5/632–635, 607–611, 600, 601

(56) References Cited

U.S. PATENT DOCUMENTS

| 3,868,103 A | | 2/1975 | Pageot et al. |
| 5,160,337 A | * | 11/1992 | Cosman ..................... 606/130 |
| 6,094,760 A | | 8/2000 | Nonaka et al. |
| 6,416,219 B1 | | 7/2002 | Pflaum et al. |
| 6,615,429 B2 | * | 9/2003 | Weil et al. ..................... 5/601 |
| 6,634,790 B1 | * | 10/2003 | Salter, Jr. .................... 378/209 |

FOREIGN PATENT DOCUMENTS

EP 0 923 922 12/1998

* cited by examiner

Primary Examiner—Edward J. Glick
Assistant Examiner—Elizabeth Keaney
(74) Attorney, Agent, or Firm—Schiff Hardin LLP

(57) ABSTRACT

A medical apparatus has a support mechanism for a treatment and/or examination subject having a support plate for the treatment and/or examination subject that is adjustable at a base and is radiation-transparent in at least one region. The support plate is seated so as to be height-adjustable at the base and adjustable around three spatial axes and is seated so as to be optionally displaceable in the longitudinal direction and/or the transverse direction in floating fashion, or displaceable by means of a connectable drive device.

6 Claims, 1 Drawing Sheet

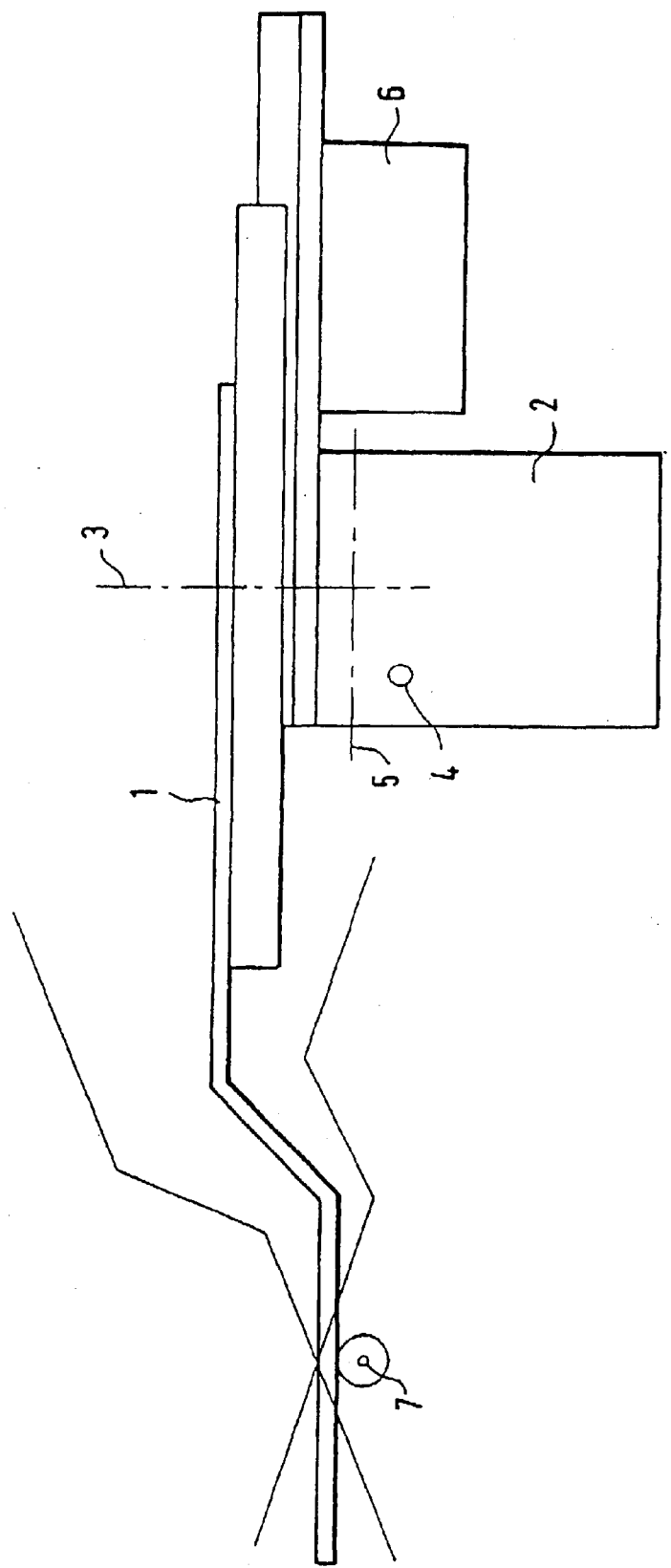

MEDICAL APPARATUS HAVING A SUPPORT TABLE FOR TREATMENT AND/OR EXAMINATION OF A SUBJECT THEREON

BACKGROUND OF THE INVENTION

1. Field of the Invention

Supporting mechanisms for a treatment subject are known that are arranged in an operating room. Such supporting mechanisms have a base at which a support plate for the treatment subject is pivotable around its longitudinal axis as well as around its transverse and which is also adjustable around a vertical axis.

2. Description of the Prior Art

For angiographic examinations, support mechanisms for an examination subject are known that have a support plate that is seated at a base so as to be adjustable along its longitudinal and transverse axis as well as height-adjustable. The support plate is radiation-transparent in at least one region, so that fluoroscopic exposures of the examination subject can be produced in conjunction with an exposure unit composed of a radiation transmitter and a radiation receiver. To this end, for example, the radiation transmitter and the radiation receiver can be seated opposite one another at the ends of a C-arm that is seated at a mount so as to be adjustable along its circumference and that is movable for example, along ceiling or floor rails.

When, after the production of, for example, X-ray exposures, an examination subject is to be treated by open surgery—as is frequently the case in angiographic examinations—then the examination subject must be transported from the angiography apparatus into the operating room and be placed on the operating table therein. Angiographic workstations are implemented such that they allow the X-ray diagnostic examination as well as the introduction of a catheter; however, they are not suited for implementing open surgery operations because the hygienic demands and the apparatus equipment are inadequate.

SUMMARY OF THE INVENTION

It is therefore an object of the invention to provide a medical apparatus which allows a good diagnosis as well as a treatment, particularly open surgery operations, without requiring a relocation of the treatment or examination subject.

This object is achieved in accordance with the invention in a medical apparatus that has a radiation source and a radiation detector and a support plate for positioning a treatment and/or examination subject relative to a radiation beam proceeding between the radiation source and detector, the support plate being adjustable at a base and being radiation-transparent in at least one region, and wherein the support plate is seated so as to be height-adjustable at the base and adjustable around three spatial axes as well as being the optionally displaceable in the longitudinal direction and/or the transverse direction in floating fashion or by means of a connectable drive device.

Such an apparatus enables the adjustment of the bearing plate as required in an operation as well as a radiation diagnosis due to the radiation transparency in conjunction with the adjustment possibility of an angiography workstation, particularly angiographic examinations, while avoiding relocating of the treatment and/or examination subject.

In an embodiment of the invention the support plate is seated so as to be pivotable around a longitudinal axis (canting axis) and around a transverse axis (tilting axis), and a drive device for pivoting around the tilting and/or canting axis is coupled to the lifting drive for the height adjustment and the drive device for the displacement of the support plate so that the support plate can be pivoted around a prescribed isocenter. It is of particular significance that pivoting ensues around a virtual swiveling axis of the isocenter of the treatment and/or examination subject that proceeds parallel to the tilting axis so that a prescribable body region can be simultaneously arranged in the isocenter and thus allowed to remain at the same location. For example, this can be the head, the heart or some other organ, specifically an organ at which surgical interventions are to ensue.

The inventive structure enables a number of different motion possibilities at a table:

- rotation (optionally manually/motorized)
- lifting motion
- canting motion
- tilting motion (optionally ±15° or −15°/+90°)
- combined tilting/canting motion
- longitudinal motion (optionally manually/motorized)
- transverse motion (optionally manually/motorized)
- combined longitudinal/transverse motion (optionally manually/motorized)
- combined lifting/tilting/longitudinal motion
- combined lifting/canting/transverse motion
- longitudinal or transverse motion (possible in every tilted position or canted position).

The support plate can be variably configured so as to form a support plate adapted for angiography, a support adapted for use in an operating room (as a flat support plate or as a support plate with at least one bend therein), or as support plate adapted for use in a computed tomography examination.

An exposure unit that can be moved from a standby position wherein free access to the bearing mechanism is possible into an exposure position for producing radiation exposures. For example, a C-arm is suitable as the common carrier for this purpose, the source and detector being respectively mounted at the opposite ends thereof. The C-arm itself can in turn be carried in a known way so as to be adjustable either at the ceiling of a room or at a floor pedestal.

The operation-diagnosis apparatus preferably has a set of interchangeable, different support plates. All support plates of the set can be attached to the base.

The set preferably includes an angiography support plate, an OP support plate and/or a computed tomography (CT) support plate.

DESCRIPTION OF THE DRAWING

The single FIGURE is a side view of a support table for treatment and/or examination of a subject in a medical apparatus, constructed in accordance with the principles of the present invention.

DESCRIPTION OF THE PREFERRED EMBODIMENTS

The inventive supporting mechanism has a partially radiation-transparent support plate 1 that is that is composed of material that can be bent. The support plate 1 is adjustably arranged at a base 2 that also can accept drive units for the adjustment of the position of the support plate. In addition to a height adjustment in the direction of the axis 3 and a pivotability of the support plate 1 around this vertical axis 3, the support plate 1 can be pivoted around a transverse axis (tilting axis 4 and around a longitudinal axis (canting axis 5) that is perpendicular thereto. All of these motions preferably ensue motorized by means of electrical or hydraulic drives. Preferably, the drives for the rotational movements are disconnectable, so that the corresponding movements can optionally ensue manually.

Additionally, of special significance for the present invention, the support plate 1 is displaceable in the longitudinal direction and in the transverse direction. This displacement can ensue with the assistance of a drive mechanism 6 (schematically shown). This drive mechanism is coupled to the support plate 1 in such a way that the drive mechanism 6 can be optionally completely disconnected, so that a floating bearing of the support plate 1 is then established that enables a simple fine adjustability and truing of the treatment and/or examination subject, given a horizontal support plate 1. Whenever the support plate 1 is tilted or canted, the drive mechanism 6 should be coupled, preferably automatically, in order to assure locking of the support plate 1 in the respective position without the necessity of separate lock mechanisms.

The drive mechanism 6 for, for example, pivoting around the tilting axis 4 can be coupled to the lifting drive for the height adjustment in the direction of the vertical axis 3 and to the drive mechanism 6 such that, by means of a program in a central control device the support plate 1 pivots around a prescribable, virtual isocenter 7 whose position likewise can be prescribed.

The cut-in of the drive mechanism 6, i.e. the connection of the support plate 1 to this drive mechanism 6 (which, of course, need not be actually activated but can act as a lock due to the cut-in without free movement), is always required before a pivot around one of the rotational axes 3, 4 and 5 ensues, i.e. the floating bearing of the support plate 1 can only be applied only when the support plate 1 resides horizontally and no tilting is to be undertaken.

Although modifications and changes may be suggested by those skilled in the art, it is the invention of the inventors to embody within the patent warranted heron all changes and modifications as reasonably and properly come within the scope of their contribution to the art.

What is claimed is:

1. In an operation-diagnosis apparatus having an exposure unit comprising a radiation receiver and a radiation transmitter and a supporting mechanism for a subject comprising a support plate, having a radiation-transparent region, adapted to receive a subject thereon and a base on which said support plate is adjustably mounted, the improvement comprising:

said support plate being mounted to said base for adjustment relative to three spatial axes;

a lifting drive in said base for height-adjustment of said support plate;

a displacement drive in said base for selective coupling to said support plate for displacing said support plate in at least one of a longitudinal direction of said support plate and a transverse direction of said support plate substantially perpendicular to said longitudinal direction, when coupled to said support plate, and allowing floating displacement of said support plate when uncoupled from said support plate;

said support plate being mounted to said base for pivoting around a canting axis and pivoting around a tilting axis parallel to said transverse direction;

a pivoting drive in said base connected to said support plate for pivoting said support plate around at least one of said canting axis and said tilting axis; and said lifting drive, said displacement drive and said pivoting drive being coupled together for pivoting said support plate around a predetermined isocenter of said support plate.

2. The improvement of claim 1 wherein said pivoting drive is capable of pivoting said support plate around at least one of said spatial axes only when said displacement drive is coupled to said support plate.

3. The improvement of claim 1 wherein said support plate has a variable configuration.

4. The improvement of claim 3 wherein said support plate is variably configurable to form a support plate adapted for angiography, a flat operating room support plate, an operating room support plate having at least one bend therein, and a support plate adapted for computed tomography.

5. The improvement of claim 1 comprising a set of interchangeable support plates, including said support plate with said radiation-transparent region.

6. The improvement of claim 5 wherein said set of support plates includes an angiography support plate, an operating room support plate, and a computed tomography support plate.

* * * * *